United States Patent [19]

Ponte et al.

[11] Patent Number: 4,666,499

[45] Date of Patent: May 19, 1987

[54] HERBICIDAL 2 METHYL-4-PHOSPHINYLCINNOLINIUM HYDROXIDE INNER SALTS

[75] Inventors: John R. Ponte; James J. Steffens; Herbert Estreicher, all of Modesto, Calif.

[73] Assignee: E. I. Du Pont de Nemours and Company, Wilmington, Del.

[21] Appl. No.: 770,463

[22] Filed: Aug. 29, 1985

[51] Int. Cl.$^4$ .................... A01N 43/58; C07D 471/02
[52] U.S. Cl. ........................................ 71/86; 544/232; 544/235; 71/87
[58] Field of Search .................... 544/232, 235; 71/86, 71/87

[56] References Cited

U.S. PATENT DOCUMENTS 3,773,766 11/1973 Schmidt et al. .................... 544/232

*Primary Examiner*—Donald G. Daus
*Assistant Examiner*—Stephen M. Kapner

[57] ABSTRACT

Certain 2-methyl-4-phosphinylcinnolinium hydroxide inner salts, useful for controlling unwanted plants.

2 Claims, No Drawings

HERBICIDAL 2 METHYL-4-PHOSPHINYLCINNOLINIUM HYDROXIDE INNER SALTS

DESCRIPTION OF THE INVENTION

It has been found that the growth of certain unwanted plants can be controlled by 2-methyl-4-phosphinylcinnolinium hydroxide inner salts described by the formula

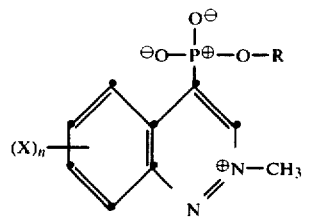

wherein R is alkyl of one to ten carbon atoms, n is zero, one or two, and X is one of halogen, nitro, polyhalomethyl, polyhalomethoxy, cyano, amino, monoalkylamino, dialkylamino, alkyl, alkoxy, alkylthio, and alkylsulfonyl wherein each alkyl moiety contains from one to four carbon atoms, and cycloalkyl of three to six carbon atoms. Any alkyl moiety present is suitably either straight-chain or branched-chain.

The preparation, isolation and testing of typical individual species of the compounds of Formula I are described in the examples, following. The class of compounds is further illustrated and exemplified by the following further individual species, all of which are specifically contemplated in this invention. In the interest of brevity, and clarity, and to avoid repetition of sometimes long chemical names, these species will be identified in terms of Formula I and the symbols used therein. The following are the species, of the subgenus wherein R is methyl:

| Species No. | (X)n (number indicates position in ring) |
|---|---|
| 11 | 7-trifluoromethyl |
| 12 | 6-fluoro |
| 13 | 6-chloro |
| 14 | 6-trifluoromethyl |
| 15 | 6-cyano |
| 16 | 6-nitro |
| 17 | 6-methoxy |
| 18 | 6-methyl |
| 19 | 6-ethoxy |
| 20 | 6-isopropoxy |
| 21 | 6-methylsulfonyl |
| 22 | 6-methylthio |
| 23 | 8-fluoro |
| 24 | 8-chloro |
| 25 | 8-trifluoromethyl |
| 26 | 8-cyano |
| 27 | 8-nitro |
| 28 | 8-methoxy |
| 29 | 8-methyl |
| 30 | 8-ethoxy |
| 31 | 8-isopropoxy |
| 32 | 8-methylsulfonyl |
| 33 | 8-methylthio |
| 34 | 5-chloro |
| 35 | 5-methyl |
| 36 | 7-methoxy |
| 37 | 7-nitro |
| 38 | 5-methoxy |

The manner in which compounds of Formula I can be prepared is illustrated in Examples 1-12 hereinafter, being readily prepared by treating the appropriate 4-(Z-sulfonyl)cinnoline (Z being alkyl or optionally-substituted phenyl):

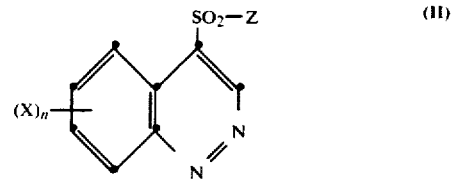

with an alkali acid salt of the appropriate (methyl) (R) diester of phosphonic acid:

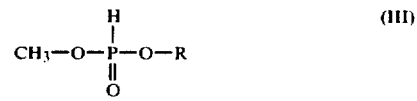

at a low temperature to form the corresponding cinnoline-4-phosphonate

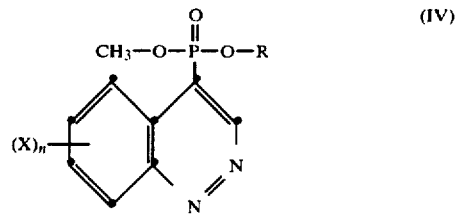

which is then heated to effect rearrangement to the corresponding compound of Formula I.

Preparation of the inner salt of Formula I is effected by adding a solution of the salt of the diester of Formula III in tetrahydrofuran to a stirred mixture of the sulfonyl-substituted cinnoline of Formula II in tetrahydrofuran, at a low temperature—suitably in the range of $-20°$ C. to $-60°$ C.—then allowing the temperature of the mixture to rise to room temperature and stirring the mixture at that temperature or somewhat above—for example, up to about 40° C.—until the rearrangement has been effected. However, a preferred procedure is to isolate the intermediate phosphate (IV), dissolve it in methanol and heat the solution until the rearrangement is complete. An often convenient technique is to heat the mixture at reflux temperature. Moisture and oxygen should be excluded from the reaction mixture. Isolation and purification of the inner salt product (I) is effected by conventional means and techniques, as shown in the Examples, herinafter.

4-sulfonyl-substituted cinnolines of Formula II are known: Japanese Pat. No. 70 25,511 (Chemical Abstracts, volume 73, abstract 131020m (1970)). Also, as shown in Example 8, hereinafter, such sulfonyl-substituted cinnolines can be prepared from the corresponding 4-hydroxycinnolines. 4-hydroxycinnolines also are known compounds: N. J. Leonard and S. N. Boyd, Jr., Journal of Organic Chemistry, volume 11, pages 419-428 (1946); K. Schofield and J. C. E. Simpson, Journal of the Chemical Society (London), 1945, pages 512-520. A facile method for preparing 4-hydroxycinnolines is the subject of application Ser. No. 737,693, filed May 28, 1985, now pending.

The following examples describe the preparation, isolation and physical properties of typical individual species of the compounds of Formula I, in particular instances. In each case, the identity of each product, and each intermediate involved, was confirmed by appropriate chemical and spectral analyses.

EXAMPLE 1

4-(Hydroxymethoxyphosphinyl)-2-methyl-cinnolinium hydroxide inner salt (1)

88.0 g of dimethyl phosphonate was added over two hours to a stirred mixture of 19.2 g of freshly hexane-washed sodium hydride and 500 ml of anhydrous THF, at 0°–5° C., in a nitrogen atmosphere. The resulting mixture was added over 1.5 hours to a stirred mixture of 199.5 g of 4-(methylsulfonyl)cinnoline (1A) and 1.1 liters of anhydrous THF, at −10° C. to 20° C. The resulting mixture was stirred at about −10° C. for one hour, then was poured over 5 liters of ice water containing 20 ml of glacial acetic acid. The resulting mixture was extracted with methylene chloride, the extract was dried (MgSO$_4$), and stripped of solvent. The residue was mixed with 400 ml of methanol and the mixture was refluxed for 6 hours. The mixture was stripped of solvent, then the residue was stirred with 1.5 liters of acetone for 20 hours. Then the mixture was filtered and the solid product was dried under reduced pressure to give 1, as a tan solid, m.p.: 172°–175° C.

EXAMPLES 2–3

The following further individual species of the compounds of Formula II were prepared, by treating 1A with the appropriate methyl R phosphonate ((CH$_3$O)(-RO)P(O)H), according to the procedures described in Example 1 for preparing 1. In the table, each species is identified in terms of the symbol R, referring to Formula I, n being zero in each case.

TABLE I

| Example No. | Compound No. | R | Physical Properties |
|---|---|---|---|
| 2 | 2 | 2,2,2-trichloroethyl | grey solid, m.p.: 198-199° C. with decomposition |
| 3 | 3 | isopropyl | green solid, m.p.: not determined |

EXAMPLE 4

4-(Hydroxymethoxyphosphinyl)-8-methoxy-2-methyl-cinnolinium hydroxide inner salt (4)

50.0 g of 3-methoxyacetophenone was added slowly, drop-by-drop, to 250 ml of 70% nitric acid at room temperature. The mixture was allowed to stand for 17 hours, warmed and held at 40° C. for 1 hour, cooled and diluted to three times its volume with water. The resulting mixture was extracted with ethyl acetate. The extract was washed with water, then with saturated sodium chloride solution, dried (Na$_2$SO$_4$) and the solvent was evaporated. The residue was dissolved in ethyl acetate, hexane was added and the mixture was set in dry ice. The solid that formed was collected and dried under reduced pressure to give 3-methoxy-2-nitroacetophenone (4A), as a cream-colored solid, m.p.: 125°–127°C.

21.95 g of 4A was suspended in 220 ml of a 1:1 v:v mixture of acetic acid and water at room temperature. Then 18.90 g of iron filings were added in portions over 0.5 hour. The mixture was refluxed for 1.5 hours and diluted with water, and the resulting mixture was extracted with ethyl acetate. The extract was washed with water, dilute aqueous sodium carbonate solution, dried (Na$_2$SO$_4$) and the solvent was evaporated. The residue was chromatographed on silica gel, using a 1:1 v:v mixture of ethyl acetate and hexane as eluent, to give 2-amino-3-methoxyacetophenone (4B), as a green solid, m.p.: 48°–49° C.

4.5 ml of concentrated hydrochloric acid was added to a suspension of 3.3 g of 4B in 20 ml of water and 20 g of ice, then a solution of 1.45 g of sodium nitrite in 10 ml of water was added, at 0° C. After 25 minutes, 40 ml of chilled methylene chloride and a solution of 16.40 g of sodium acetate in 40 ml of water was added. The mixture was stirred at −12° C. overnight, filtered and the collected solid was dried under reduced pressure to give 4-hydroxy-8-methoxycinnoline (4C), as a brown solid, m.p.: 160°–163° C.

A mixture of 1.80 g of 4C, 1.93 g of phosphorus pentachloride and 2.8 ml of phosphorus oxychloride was held at 100° C., under nitrogen, for 30 minutes. The resulting mixture was cooled, mixed with 100 ml of ice water and brought to pH=4 with sodium acetate, and extracted with ether. The extract was washed, successively, with water, dilute aqueous sodium carbonate, water, and saturated aqueous sodium chloride solution, dried (Na$_2$SO$_4$) and the solvent was evaporated. The residue was dissolved in 20 ml of dry dimethylformamide (DMF), under nitrogen, and, at 0° C., 1.02 g of sodium p-toluenesulfinate was added. The mixture was allowed to warm to and held at room temperature for 27 hours, then was diluted with water and filtered. The solid was dried under reduced pressure to give 4-(p-methylphenylsulfonyl)-8-methoxycinnoline (4D) as a brown-yellow solid, m.p.: 152.5°–155° C., with decomposition.

0.13 g of hexane-washed sodium hydride was suspended in 1 ml of dry THF under nitrogen, then at 5° C., a solution of 0.30 g of dimethyl phosphonate in 2 ml of dry THF was added, drop-by-drop. After 45 minutes, the resulting mixture was added to a mixture of 0.87 g of 4D and 10 ml of dry THF at −60° C. The mixture was allowed to warm to 0° C. and held at that temperature for 28 hours. The mixture then was diluted to three times its volume with water and the resulting mixture was extracted with ethyl acetate. The extract was washed with water, saturated aqueous sodium chloride solution, dried (Na$_2$SO$_4$), and the solvent was evaporated. The residue was flash chromatographed on silica gel, using first a 1:1 v:v mixture of methylene chloride and ethyl acetate, then ethyl acetate alone, as eluents. The ethyl acetate eluate was stripped of solvent and the residue was dissolved in methanol. The solution was held at room temperature for 18 hours, then refluxed for 11 hours. The solution was cooled and the solvent was evaporated. The residue was triturated with ether. The residue was dissolved in methylene chloride, the solution was filtered, part of the solvent was evaporated, then hexane was added, to give a solid product, identified as 4, as a green solid, m.p. 165.5°–166.5° C., with decomposition.

EXAMPLES 5-7

By the procedures described in Examples 1 and 4, the following further individual species of the compounds of Formula I were prepared from the appropriate precursor methyl R phosphonates and 1A.

| Example No. | Compound No. | R | Physical Properties |
|---|---|---|---|
| 5 | 5 | ethyl | grey solid, m.p.: 157–159° C., with decomposition |
| 6 | 6 | n-butyl | tan solid, m.p.: 142.5–143° C. with decomposition |
| 7 | 7 | cyclohexyl | green solid, m.p.: 193–194° C. with decomposition |

EXAMPLE 8

By the procedures described in Example 4, 4-(hydroxymethoxyphosphinyl)-8-ethoxy-2-methyl-cinnolinium hydroxide inner salt (8), was prepared as a yellow solid, m.p.: not determined, from 3-ethoxyacetophenone.

EXAMPLE 9

4-(hydroxymethoxyphosphinyl)-6,7-dimethyl-2-methyl-cinnolinium hydroxide inner salt (9)

95 ml of acetic anhydride was added to a stirred solution of 3,4-dimethylaniline in 300 ml of glacial acetic acid at such a rate the temperature of the mixture slowly rose to 60° C. The resulting mixture was stirred while the temperature dropped to room temperature, then evaporated to dryness. A mixture of water and ice was added to the residue, followed by methylene chloride. The resulting mixture was stirred and treated with solid sodium bicarbonate until neutral. The organic phase was separated, and dried (MgSO$_4$), and the solvent was evaporated to give 3,4-dimethylacetanilide (9A).

105 ml of acetyl chloride was added to a solution of 130 g of 9A in 1040 ml of carbon disulfide, then 410 g of aluminum chloride was slowly added to the stirred mixture. The mixture was stirred at reflux for 1.5 hours, cooled and the carbon disulfide phase was decanted. The remainder was poured onto ice, and the resulting precipitate was collected, washed with water and dried to give 2-acetyl-4,5-dimethylacetanilide (9B).

A mixture of 44 g of 9B and 300 ml of concentrated hydrochloric acid was refluxed for 30 minutes, then cooled in an ice bath and filtered. The collected solids were partitioned between methylene chloride and a saturated aqueous solution of sodium bicarbonate. The methylene chloride phase was separated and dried (MgSO$_4$), and the solvent was evaporated under reduced pressure. The residue was recrystallized from a 2:1 v:v mixture of hexane and ethyl acetate to give 2-amino-4,5-dimethylacetophenone (9C).

10.5 g of 9C was dissolved in 30 ml of concentrated hydrochloric acid kept cold with an ice bath, then 50 ml of water was added and the resulting mixture was treated at about 0° C. with sodium nitrite until the diazotation was complete by iodine-starch reaction. The resulting mixture was poured onto an ice-cold mixture of 50 g of sodium acetate, 150 ml of water, 50 g of ice and 50 ml of methylene chloride, and the mixture was stirred overnight, spontaneously warming to room temperature. The resulting mixture was filtered, the collected solid was washed with methylene chloride, then water, and dried in a vacuum oven. The product was recrystallized from ethanol to give 6,7-dimethyl-4-hydroxycinnoline (9D) as orange crystals, m.p.: above 260° C.

9 was prepared, as a green-white solid, m.p.: 181°–183° C., from 9D, by the procedures described in Example 5 for preparing 4 from 4C.

EXAMPLE 10

4-(hydroxymethoxyphosphinyl)-7,8-dimethyl-2-methylcinnolinium hydroxide inner salt (10)

22.3 ml of concentrated hydrochloric acid was added drop-by-drop to a stirred suspension of 2-amino-3,4-dimethylacetophenone (A. Brandstrom and S. A. I. Carlson, Acta Chemica Scandinavica, volume 21, pages 983–992 (1967)), 100 ml of water and 100 g of ice at 0° C. The resulting mixture was stirred at 0° C. for 15 minutes, then a solution of 7.8 g of sodium nitrite in 60 ml of water was added drop-by-drop over 2 minutes, at 0° C. The mixture was stirred for 40 minutes at 0° C., then 200 ml of ice-cold methylene chloride and 200 ml of an ice-cold aqueous solution containing 81.5 g of sodium acetate were added. The mixture was stirred for 6 hours at 0° C., allowed to warm gradually to room temperature, then filtered. The collected solid material was dried by azeotroping with toluene and recrystallized from ethanol-hexane to give 7,8-dimethyl-4-hydroxycinnoline 10A, as a tan solid, m.p.: above 260° C.

10 was prepared, as a yellow solid, m.p.: 205°–206° C. (with decomposition), from 10A by the procedures described in Example 5 for preparing 4 from 4C.

Compounds of Formula I have been found to affect adversely the growth of some plants, many of which are commonly considered as weeds, and therefore to be useful for controlling the growth of such unwanted plants. Compounds of Formula I have been found to have a broad spectrum of activity—i.e., to affect adversely a wide variety of species of plants. Further, while compounds of Formula I appear to have some activity when applied preemergence or preplant incorporated (applied to the soil before the seeds have sprouted), most appear to be more effective when applied postemergence (applied to the foliage of the growing plant).

For application, a compound of Formula I ordinarily is applied most effectively by formulating it with a suitable inert carrier or surface-active agent, or both. The invention, therefore, also includes compositions suitable for combatting unwanted plants, such compositions comprising an inert carrier or surface-active agent, or both, and as active ingredient at least one compound of Formula I.

The term "carrier" as used herein means an inert solid or liquid material, which may be inorganic or organic and of synthetic or natural origin, with which the active compound is mixed or formulated to facilitate its application to the plant, seed, soil or other object to be treated, or its storage, transport and/or handling. Any of the materials customarily employed in formulating pesticides, herbicides, or fungicides—i.e., horticulturally acceptable carriers—are suitable.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, superphosphates; and ground, naturally-occurring, fibrous materials, such as ground corncobs.

Examples of suitable liquid carriers are water, alcohols such as isopropyl alcohol and glycols; ketones such as acetone, methyl ethyl ketone, methyl isobutyl ketone and cyclohexanone; ethers such as cellosolves; aromatic hydrocarbons such as benzene, toluene and xylene; petroleum fractions such as kerosene, light mineral oils; chlorinated hydrocarbons such as carbon tetrachloride, perchloroethylene and trichloromethane. Also suitable are liquefied, normally vaporous and gaseous compounds. Mixtures of different liquids are often suitable.

The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium and calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, of sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usually compounded to contain 25 to 75% by weight of active compound and usually contain, in addition to the solid carrier, 3–10% by weight of a dispersing agent, 2–15% of a surface-active agent and, where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5–10% by weight of the active compound. Granules are usually prepared to have a size between 10 and 100 BS mesh (1.676–0.152 mm), and may be manufactured by agglomeration or impregnation techniques. Generally, granules will contain 0.5–25% by weight of the active compound, 0–1% by weight of additives such as stabilizers, slow release modifiers and binding agents. Emulsifiable concentrates usually contain, in addition to the solvent and, when necessary, cosolvent, 10–50% weight per volume of the active compound, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight of the active compound, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the active compound is substantially insoluble; certain organic solids or inorganic salts may be dissolved in the carrier to assist in preventing sedimentation or an antifreeze agents for water.

Of particular interest in current practice are water-dispersible granular formulations. These are in the form of dry, hard granules that are essentially dust-free, and are resistant to attrition on handling, thus minimizing the formation of dust. On contact with water, the granules readily disintegrate to form stable suspensions of the particles of active material. Such formulations contain 90% or (up to 95%) more by weight of finely divided active material, 3–7% by weight of a blend of surfactants, which act as wetting, dispersing, suspending and binding agents, and may contain up to 3% by weight of a finely divided carrier, which acts as a resuspending agent.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have thick, mayonnaise-like consistency.

It is evident from the foregoing that this invention contemplates compositions containing as little as about 0.5% by weight to as much as about 95% by weight of a compound of Formula I as the active ingredient.

The compositions of the invention may also contain other ingredients, for example, other compounds possessing pesticidal, especially insecticidal, acaricidal, herbicidal or fungicidal properties, as are appropriate to the intended purpose.

Protection of a locus or area from undesirable plants is effected by applying a compound of Formula I, ordinarily in a composition of one of the aforementioned types, to soil in which the seeds of the unwanted plants are present, or to the foliage of the unwanted plants. The active compound, of course, is applied in an amount sufficient to exert the desired action.

The amount of the compound of the invention to be used in combatting undesired plants will naturally depend on the condition of the plants, the degree of activity desired, the formulation used, the mode of application, the climate, the season of the year, and other variables. Recommendations as to precise amounts are, therefore, not possible. In general, however, application to the locus to be protected of from 0.1 to 10.0 kg per hectare of the compound of Formula I will be satisfactory.

EXAMPLES OF ACTIVITY WITH RESPECT TO PLANTS

In the following examples, the species of plants that were tested were:
Barnyardgrass (watergrass)-*Echinochloa crus-galli*

Large crabgrass-*Digitaria sanguinalis*
Downy brome-*Bromus tectorum*
Yellow foxtail-*Setaria lutescens*
Redroot pigweed-*Amaranthus retroflexus*
Velvetleaf-*Abutilon therophrasti*
Garden cress-*Lepidium sativum*
Johnson grass-*Sorghum halepense*
Morningglory-*Ipomoea sp.*

TEST PROCEDURES

The preemergence (soil) herbicidal activity of compounds of Formula I was evaluated by planting seeds of barnyardgrass, garden cress, downy brome, velvetleaf, yellow foxtail, and morningglory in test tubes, nominally measuring 25×200 millimeters, filled about three-quarters full of untreated soil, in each case covered on top with about 2.5 cubic centimeters of soil treated with a certain amount of the test compound. The treated soil applied to the tubes containing the barnyardgrass and cress seeds contained one milligram of the test compound per tube, and contained 0.1 milligram of the test compound per each tube containing the seeds of the other plants. The dosages were approximately 20 and 2.0 pounds of test compound per acre, respectively. The seeds were planted on top of the treated soil and covered with about 1.5 cubic centimeters of untreated soil. The planted soil was held under controlled conditions of temperature, moisture, and light for 9 to 10 days. The amounts of germination and growth in each tube were evaluated on a 0 to 9 scale, the numeric ratings having the following meanings:

| Rating | Meaning |
|---|---|
| 9 | No living tissue |
| 8 | Plant severely damaged and expected to die |
| 7 | Plant badly damaged, but expected to live |
| 6 | Moderate damage, but complete recovery expected |
| 5 | Intermediate damage (probably unacceptable for crop plants) |
| 3–4 | Observable damage |
| 1–2 | Plant slightly affected, possibly by the chemical, possibly due to biological variability |
| 0 | No visible effect |

The postemergence (foliar) herbicidal activity of compounds of Formula I was evaluated by spraying 10-day-old large crabgrass plants, 13-day-old pigweed plants, 6-day-old johnsongrass plants, 9-day-old velvetleaf plants, 9-day-old yellow foxtail plants and 5-day-old morningglory plants to runoff with a liquid formulation of the test compound. The crabgrass and pigweed plants were sprayed with 2.4 milliliters of a 0.25% solution (about ten pounds of the test compound per acre), and other plants were sprayed with 2.4 milliliters of a 0.025% solution (about one pound of the test compound per acre). The sprayed plants were held under controlled conditions of temperature, moisture and light for 7 to 8 days, when the effect of the test compound was evaluated visually, the results being rated on the 0 to 9 scale described above.

TABLE I

HERBICIDAL ACTIVITY

| Compound | Preemergence ||||||  Postemergence ||||||
|---|---|---|---|---|---|---|---|---|---|---|---|---|
| | Barnyard-grass | Garden Cress | Downy Brome | Velvet-leaf | Yellow Foxtail | Morning-glory | Crab-grass | Pig-weed | Johnson-grass | Velvet-leaf | Yellow Foxtail | Morning-glory |
| 1 | 9 | 9 | 9 | 7 | 7 | 7 | 9 | 9 | 9 | 9 | 9 | 9 |
| 2 | 8 | 9 | 2 | 4 | 3 | 6 | 8 | 9 | 5 | 5 | 8 | 8 |
| 3 | 8 | 9 | 5 | 5 | 3 | 5 | 9 | 9 | 9 | 7 | 7 | 7 |
| 4 | 9 | 7 | 3 | 3 | 3 | 4 | 9 | 9 | 9 | 8 | 9 | 9 |
| 5 | 9 | 9 | 4 | 7 | 7 | 9 | 9 | 9 | 9 | 7 | 9 | 9 |
| 6 | 9 | 9 | 4 | 6 | 5 | 6 | 9 | 9 | 8 | 5 | 9 | 7 |
| 7 | 8 | 9 | 2 | 3 | 2 | 3 | 9 | 9 | 8 | 3 | 5 | 8 |
| 8 | 6 | 4 | 0 | 0 | 3 | 3 | 7 | 9 | 7 | 2 | 6 | 8 |
| 9 | 8 | 5 | 3 | 2 | — | 3 | 9 | 9 | 9 | 5 | 9 | 6 |
| 10 | 2 | 4 | 0 | 2 | 0 | 2 | 9 | 9 | 6 | 3 | 6 | 6 |

EXAMPLES OF SELECTIVITY

In the following examples, the species of plants that were tested were:

| | Abbreviation |
|---|---|
| Barnyardgrass | BYRG |
| Downy Brome | DOBR |
| Johnsongrass | JOGR |
| Wild oats - *Avena fatua* | WIOA |
| Yellow foxtail | YEFT |
| Goose grass - *Eleusine indica* | GOGR |
| Yellow nutsedge - *Cyperus esculentus* | YENS |
| Cocklebur - *Xanthum pennsylvanicum* | COCB |
| Morningglory | MOGL |
| Wild mustard - *Brassica kaber* | WIMU |
| Redroot pigweed | RRPW |
| Sicklepod - *Cassia obtusifolia* | SIPO |
| Velvetleaf | VELE |
| Corn - *Zea mays* | CORZ |
| Cotton - *Gossypium hirsutum* | COTZ |
| Rice - *Oryza sativa* | RICZ |
| Grain sorghum - *Sorghum vulgare* | GRSO |
| Soybeans - *Glycine max* | SOBE |
| Sugarbeets - *Beta vulgaris* | SUBE |
| Wheat - *Triticum aestivum* | WHEZ |
| Nightshade - *Solanum sp.* | NISH |
| Field Bindweed - *Convolvulus arvensis* | FIBW |
| Hemp sesbania - *Sesbania exaltata* | HESE |
| Annual ryegrass - *Lolium multiflorum* | ANRG |
| Canada thistle - *Cirsium arvense* | CATH |
| Honey mesquite - *Prosopis glanulosa* | HOMQ |
| Giant foxtail - *Setaria faberi* | GIFT |
| Texas panicum - *Panicum texanum* | TEPA |

TEST PROCEDURES

The preemergence activity of Formula I was further determined with respect to certain species of crop plants and common species of weeds, by spraying a formulation of the test compound on soil in small pots in which seeds of the plants had been sown. The postemergence herbicidal activity of compounds of Formula I was evaluated with respect to the crop plants and weeds, by spraying a formulation of the test compound on the foliage of the young growing plants. In each series of tests, the plants were grown in pots placed in narrow trays and sprayed with the formulation. The results of the tests were evaluated on the basis of the 0–9 scale described with respect to the earlier tests. Activity of the test compound in such case was characterized as follows:

| Activity Level | Dosage (lb/acre) | Rating (one or another) |
|---|---|---|
| A - Highly Active | 0.25 | 8-9 |
|  | 1.0 | 8-9 |
|  | 2.0 | 8-9 |
| B - Very active | 0.25 | 6-7 |
|  | 1.0 | 8-9 |
|  | 2.0 | 8-9 |
| C - Active | 0.25 | 4-5 |
|  | 1.0 | 5-7 |
|  | 2.0 | 7-9 |
| D - Slightly active | 0.25 | 2-3 |
|  | 1.0 | 3-4 |
|  | 2.0 | 4-6 |
| E - Essentially inactive | 0.25 | 0-1 |
|  | 1.0 | 0-3 |
|  | 2.0 | 1-3 |

Compounds 1 and 5 were tested preemergence: Compound 1 was very active with respect to sicklepod; slightly active with respect to cotton, rice, grain sorghum, barnyardgrass, downy brome, johnsongrass, wild oats, yellow foxtail, morningglory and mustard; and essentially inactive with respect to all of the other species of test plants.

Compound 5 was active with respect to barnyardgrass; slightly active with respect to corn, cotton, rice, grain sorghum sugar-beets, downy brome, johnsongrass, wild oats, yellow foxtail, morningglory, mustard, pigweed, sicklepod and velvetleaf; and essentially inactive with respect to all of the other species of test plants.

All of Compounds 1 through 10 were tested postemergence. Table II sets forth the results of the tests.

TABLE II

| Plant Species | Activity Level | Numbers of the Compounds Having the Activity Level |
|---|---|---|
| BYGR | A | 4, 5, 9 |
|  | B | 1, 3, 6, 8 |
|  | C | 2, 7, 10 |
| DOBR | C | 1, 9 |
|  | D | 2, 4, 5, 6, 10 |
|  | E | 3, 7, 8 |
| JOGR | A | 3, 4, 5, 9 |
|  | B | 1, 6, 7, 10 |
|  | C | 8 |
|  | D | 2 |
| WIOA | D | 4, 5, 8, 9, 10 |
|  | E | 1, 2, 3, 6, 7 |
| YEFT | A | 3, 4, 5, 6 |
|  | B | 1, 8, 9 |
|  | C | 7 |
|  | D | 2, 10 |
| GOGR | A | 1 |
|  | B | 3, 4, 5, 7 |
|  | D | 2, 6, 8 |
| YENS | D | 5, 9, |
|  | E | 1, 2, 3, 4, 6, 7, 8, 10 |
| HOMQ | B | 3 |
|  | C | 4, 5, 7, 9, 10 |
|  | D | 2, 6, 8 |
| COCB | A | 3, 5 |
|  | B | 1, 4, 6, 7, 8 |
|  | D | 2, 9, 10 |
| MOGL | A | 1, 3, 4, 5, 7 |
|  | B | 8, 9 |
|  | C | 6, 10 |
|  | D | 2 |
| WIMU | A | 1, 2, 3, 5, 6, 7 |
|  | B | 4, 8 |
|  | C | 9 |
| RRPW | D | 10 |
|  | A | 1, 2, 3, 4, 5, 6, 7, 8, 9, |
|  | C | 10 |
| SIPO | A | 1, 3, 4, 5, 6, 7, 8, |
|  | B | 2 |
|  | C | 9, 10 |
| VELE | A | 5 |
|  | B | 1, 3, 4 |
|  | C | 7, 9 |
|  | D | 2, 6, 8, 10 |
| NISH | A | 3, 4, 5, 6, 8 |
|  | B | 1, 7 |
|  | C | 2, 9 |
|  | D | 10 |
| TEPA | B | 9 |
|  | C | 10 |
| GIFT | B | 9, 10 |
| CATH | D | 9 |
|  | E | 10 |
| FIBW | B | 4 |
|  | C | 9 |
|  | D | 2, 8, 10 |
|  | E | 6 |
| ANGR | D | 9, 10 |
| HESE | C | 9 |
|  | D | 10 |
| CORZ | A | 3 |
|  | B | 1, 5, 7, 10 |
|  | C | 2, 4, 9 |
|  | D | 6, 8 |
| COTZ | A | 1, 3, 4, 5, 7 |
|  | B | 8, 9, 10 |
|  | C | 2, 6 |
| RICZ | C | 4 |
|  | D | 1, 3, 5, 7, 9, 10 |
|  | E | 2, 6, 8 |
| GRSO | A | 1, 5 |
|  | B | 4, 9 |
|  | C | 3, 6, 10 |
|  | D | 2, 7, 8 |
| SOBE | A | 3, 4, 5 |
|  | B | 7, 9 |
|  | C | 1, 2, 6 |
|  | D | 8, 10 |
| SUBE | A | 1, 3, 4, 5 |
|  | C | 7, 9 |
|  | D | 2, 8, 10 |
|  | E | 6 |
| WHEZ | C | 4 |
|  | D | 1, 2, 3, 5, 6, 7, 9 |
|  | E | 8, 10 |

We claim:

1. A compound of the formula:

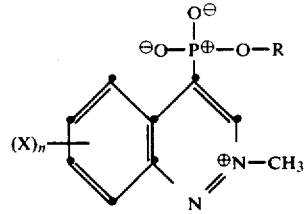

wherein R is alkyl of one to three carbon atoms, n is zero, one or two, and X is one of halogen, nitro, polyhalomethyl, polyhalomethoxy, cyano, amino, monoalkylamino, dialkylamino, alkyl, alkoxy, alkylthio and alkylsulfonyl wherein each alkyl moiety has from one to four carbon atoms, and cycloalkyl of three to six carbon atoms.

2. A method for controlling unwanted plants at a locus, that method comprising applying to the locus an effective amount of a compound of claim 1.

* * * * *